(12) United States Patent
Yu et al.

(10) Patent No.: US 7,371,570 B2
(45) Date of Patent: May 13, 2008

(54) CELL-SPECIFIC ADENOVIRUS VECTOR COMPRISING EBV-SPECIFIC PROMOTER

(75) Inventors: De Chao Yu, Foster City, CA (US); Nagarajan Ramesh, Santa Clara, CA (US)

(73) Assignee: Cell Genesys, Inc., South Francisco, CA (US)

( * ) Notice: Subject to any disclaimer, the term of this patent is extended or adjusted under 35 U.S.C. 154(b) by 533 days.

(21) Appl. No.: 10/698,160

(22) Filed: Oct. 30, 2003

(65) Prior Publication Data

US 2004/0171159 A1    Sep. 2, 2004

Related U.S. Application Data

(60) Provisional application No. 60/423,203, filed on Nov. 1, 2002.

(51) Int. Cl.
C12N 15/861 (2006.01)
C12N 5/10 (2006.01)
A61K 48/00 (2006.01)

(52) U.S. Cl. .................. 435/320.1; 435/325; 536/23.1; 536/24.1

(58) Field of Classification Search ...................... None
See application file for complete search history.

(56) References Cited

U.S. PATENT DOCUMENTS

| | | | |
|---|---|---|---|
| 5,998,205 | A | 12/1999 | Hallenbeck et |
| 6,432,700 | B1 | 8/2002 | Henderson et |
| 6,551,587 | B2 | 4/2003 | Hallenbeck et |
| 6,638,762 | B1 | 10/2003 | Chang et al. |
| 6,692,736 | B2 | 2/2004 | Yu et al. |
| 2001/0006633 | A1 | 7/2001 | Kirn |
| 2001/0053768 | A1 | 12/2001 | Gregory et al. |
| 2003/0026789 | A1 | 2/2003 | Gregory et al. |
| 2003/0068307 | A1 | 4/2003 | Yu et al. |
| 2003/0104625 | A1 | 6/2003 | Cheng et al. |
| 2004/0009588 | A1 | 1/2004 | Chang et al. |

FOREIGN PATENT DOCUMENTS

| | | |
|---|---|---|
| WO | WO 92/03563 | 3/1992 |
| WO | WO 96/17053 | 6/1996 |
| WO | WO 98/29555 | 7/1998 |
| WO | WO 98/39464 | 9/1998 |
| WO | WO 96/34969 | 11/1998 |
| WO | WO 99/25860 | 5/1999 |
| WO | WO 99/28469 | 6/1999 |
| WO | WO 99/58604 | 11/1999 |
| WO | WO 01/36650 | 5/2001 |
| WO | WO 01/72341 | 10/2001 |
| WO | WO 01/73093 | 10/2001 |
| WO | WO 02/067861 | 9/2002 |

OTHER PUBLICATIONS

Chen et al., Linkage Between Stat Regulation and Epstein-Barr Virus Gene Expression in Tumors, J. Virol., 2001, 75(6): 2929-2937.
Chia et al., A Novel Conditionally Oncolytic Adenovirus for the Treatment of Nasopharyngeal Carcinoma (NPC), Proc. Amer. Ass. For Cancer Res., 2002, 43: 1098-1099.
Chiocca et al., Oncolytic Viruses, Nature Publishing Group, 2002, 2: 938-951.
Feng et al., Use of Adenovirus Vectors Expressing Epstein-Barr Virus (EBV) Immediate-Early Protein BZLF1 or BRLF1 to Treat EBV-Positive Tumors, J Virol., 2002, 76(21):10951-10959.
Grinstein et al., Demonstration of Epstein-Barr Virus in Carcinomas of Various Sites, Cancer Res., 2002, 1:62(17):4876-4878.
Li et al., Tumor-Targeted Gene Therapy for Nasopharyngeal Carcinoma, Cancer Res., 2002, 62: 171-178.
Reisman et al., Trans Activation of an Epstein-Barr Viral Transcriptional Enhancer by the Epstein-Barr Viral Nuclear Antigen 1, Molecular and Cell. Biol., 1986, 6(11): 3838-3846.
Sadler et al., The Epstein-Barr Virus 3.5-Kilobase Latent Membrane Protein 1 MRNA Initiates From a Tata-Less Promoter Within the First Terminal Repeat, J. of Virol., 1995, 69(7): 4577-4581.
Sjöblom et al., An ATF/CRE Element Mediates Both EBNA2-Dependent and EBNA2-Independent Activation of the Epstein-Barr Virus LMP1 Gene Promoter, J. of Virol., 1998, 72(2): 1365-1376.
Tsai et al., Additive Effect of SP1 and SP3 in Regulation of the ED-L1E Promoter of the EBV LMP 1 Gene in Human Epithelial Cells, Virology, 1999, 261: 288-294.
Yu et al., Selectively Replicating Oncolytic Adenoviruses as Cancer Therapeutics, Curr. Opinion in Mol. Ther., 2002, 4(5): 435-443.
Waehler et al., Experimental Gene Therapy of Hepatocellular Carcinoma: Expression of IL-12, 4-1BBL and IL-2 From a Single Adenoviral Vector, 10th Annual ESGT meeting, Oct. 13-16, 2002.

*Primary Examiner*—David Guzo
(74) *Attorney, Agent, or Firm*—Ropes & Gray, LLP; James F. Haley, Jr.

(57) ABSTRACT

Replication-competent adenoviral vectors comprising an EBV-specific transcriptional regulatory element (TRE) operably linked to a gene required for adenovirus replication are provided. By providing for transcriptional initiating regulation dependent upon transcription factors that are only active in specific, limited cell types, virus replication can be restricted to particular target cells. The modified adenovirus may be used as a vehicle for introducing new genetic capability, particularly associated with cytotoxicity for treating neoplasia.

16 Claims, 2 Drawing Sheets

CELL-SPECIFIC ADENOVIRUS VECTOR COMPRISING EBV-SPECIFIC PROMOTER

BACKGROUND OF THE INVENTION

The Epstein-Barr virus (EBV) has been implicated in a number of human tumors, and is of interest in the development of anti-tumor therapies. EBV associated diseases often arise from a failure of the host immune response to control the proliferation of latently infected cells. During the persistent stage of EBV infection, the virus primarily infects long-lived memory B cells in the periphery. Latent EBV infection of B cells is associated with rapid tumor development in immunocompromised individuals, such as bone marrow transplant recipients and persons with AIDS.

Burkitt's lymphoma (BL) has likewise been linked to immunosuppression in AIDS, and to malarial infection in the case of endemic BL. All cases of Burkitt's lymphoma are also marked by the presence of specific chromosomal translocations, which result in the activation of the c-myc proto-oncogene. The majority of these involve a reciprocal translocation between chromosome 8 at or near the site of the c-myc locus, and the immunoglobulin heavy chain locus on chromosome 14. Other EBV associated tumors include Hodgkin's disease, certain unusual types of T cell lymphoma, and nasopharyngeal carcinoma.

EBV is a gamma herpesvirus of the *Lymphocryptovirus* (LCV) genus. The EBV genome is composed of linear double-stranded DNA, approximately 172 kilobase pairs (kb) in length. EBV has a series of 0.5 kb terminal direct repeats and internal repeat sequences that divide the genome into short and long, largely unique sequence domains. EBV was the first herpesvirus to have its genome completely cloned and sequenced. There are two major types of EBV isolate, called types 1 and 2, which appear to be identical over the bulk of the EBV genome but show allelic polymorphism in a subset of latent genes, including EBNA-LP.

EBV infects the majority of the World's adult population and following primary infection the individual remains a lifelong carrier of the virus. In underdeveloped countries, primary infection with EBV usually occurs during the first few years of life and is often asymptomatic. However, in developed populations, primary infection is more frequently delayed until adolescence or adulthood, in many cases producing the characteristic clinical features of infectious mononucleosis. EBV is orally transmitted, and infectious virus can be detected in oropharyngeal secretions from infectious mononucleosis patients, from immunosuppressed patients and at lower levels from healthy EBV seropositive individuals. Early in the course of primary infection, EBV infects B-lymphocytes. EBV does not usually replicate in B-lymphocytes but instead establishes a latent infection, which is characterized by the limited expression of a subset of virus genes.

Several viruses have recently come forth as both vehicles for gene therapy and as candidate anticancer agents. Among them adenovirus, a mildly pathogenic human virus that propagates prolifically in epithelial cells, the origin of many human cancers. Adenovirus has emerged as a virus that can be engineered with oncotropic properties. See, for example, U.S. Pat. Nos. 5,846,945; 5,801,029; 5,747,469; PCTUS1999/08592 (WO 99/59604;) or PCT/US1998/03514 (WO 98/35554;); PCT/US1997/22036 (WO 98/29555;). Replication competent adenovirus vectors have been designed to selectively replicate in tumor cells. Improving the delivery of these adenoviruses, both to locoregional and disseminated disease, as well as improving the virus to promote intratumoral spread are of particular interest.

Several experimental cancer therapies utilize various aspects of adenovirus or adenovirus vectors. See, for example, U.S. Pat. Nos. 5,846,945; 5,801,029; PCT/US99/08592; U.S. Pat. No. 5,747,469; PCT/US98/03514; and PCT/US97/22036.

Although replication competent adenoviruses are able to achieve selective targeting and amplification for the treatment of some types of cancer, there remains a need for improvement in both the adenovirus vectors themselves and methods for their use with respect to particular types of cancers. Preliminary results suggest that effective treatment strategies may require development of specific adenovirus vectors and/or methods particular to the type of cancer under treatment.

There is, therefore, substantial interest in development of viral vectors that enable the targeting of EBV-positive cells in vivo. The uniform presence of the EBV genome in certain tumors, versus its presence in only a very small number of normal B cells, suggests that novel therapies which include specific targeting and cytolysis of EBV-positive cells may be effective for treating such tumors.

Publications

Feng et al. (2002) *J. Virol.* 76:10951-10959 discuss the use of adenovirus vectors expressing EBV immediate early proteins to treat EBV-positive tumors. Abdulkarim and Bourhis (2001) *Lancet Oncol.* 2:622-630 suggest that the use of antisense oligodeoxynucleotides against Epstein-Barr virus and human papillomavirus oncoproteins to effect downregulation of the oncoproteins can influence tumor cell growth and restore sensitivity to cytotoxic agents. Another approach uses antiviral drugs such as acyclic nucleoside phosphonates, in combination with chemotherapy.

Grinstein et al. (2002) *Cancer Res* 62(17):4876-8 suggest the presence of EBV in a variety of carcinomas, including those of the breast, lung, colon, and prostate. A review of EBV in human disease may be found in Murray and Young (2002) *Frontiers in Bioscience* 7:519-540.

SUMMARY OF THE INVENTION

The present invention provides replication-competent adenoviral vectors comprising an EBV-specific transcriptional regulatory element (TRE) operably linked to a gene required for adenovirus replication. In one aspect, the EBV specific TRE is derived from the sequence upstream of the translational start codon for the LMP1, LMP2A or LMP2B genes, presented herein as SEQ ID NO:1-2, respectively. The EBV-specific TRE may comprise one or more regulatory sequences, e.g. enhancers, promoters, transcription factor binding sites and the like, which may be derived from the same or different genes.

The adenovirus vectors may comprise co-transcribed first and second adenoviral genes under control of an EBV-specific TRE, where the second gene may be under translational control of an internal ribosome entry site (IRES). Methods are provided for introducing into a cell an adenoviral vector comprising an EBV-specific TRE operably linked to a gene required for virus replication, and host cells comprising the adenovirus vector(s). In another aspect, methods are provided for conferring selective cytotoxicity in target cancer cells associated with EBV, including Burkitt's lymphoma, Hodgkin's Disease, nasopharyngeal carcinoma, and lymphoproliferative diseases, the method comprising contacting the cells with an adenovirus vector of the invention, whereby the vector enters the cell and propagates virus, which propagation results in the lysis of the host cell.

DETAILED DESCRIPTION OF THE EMBODIMENTS

Figure 1:
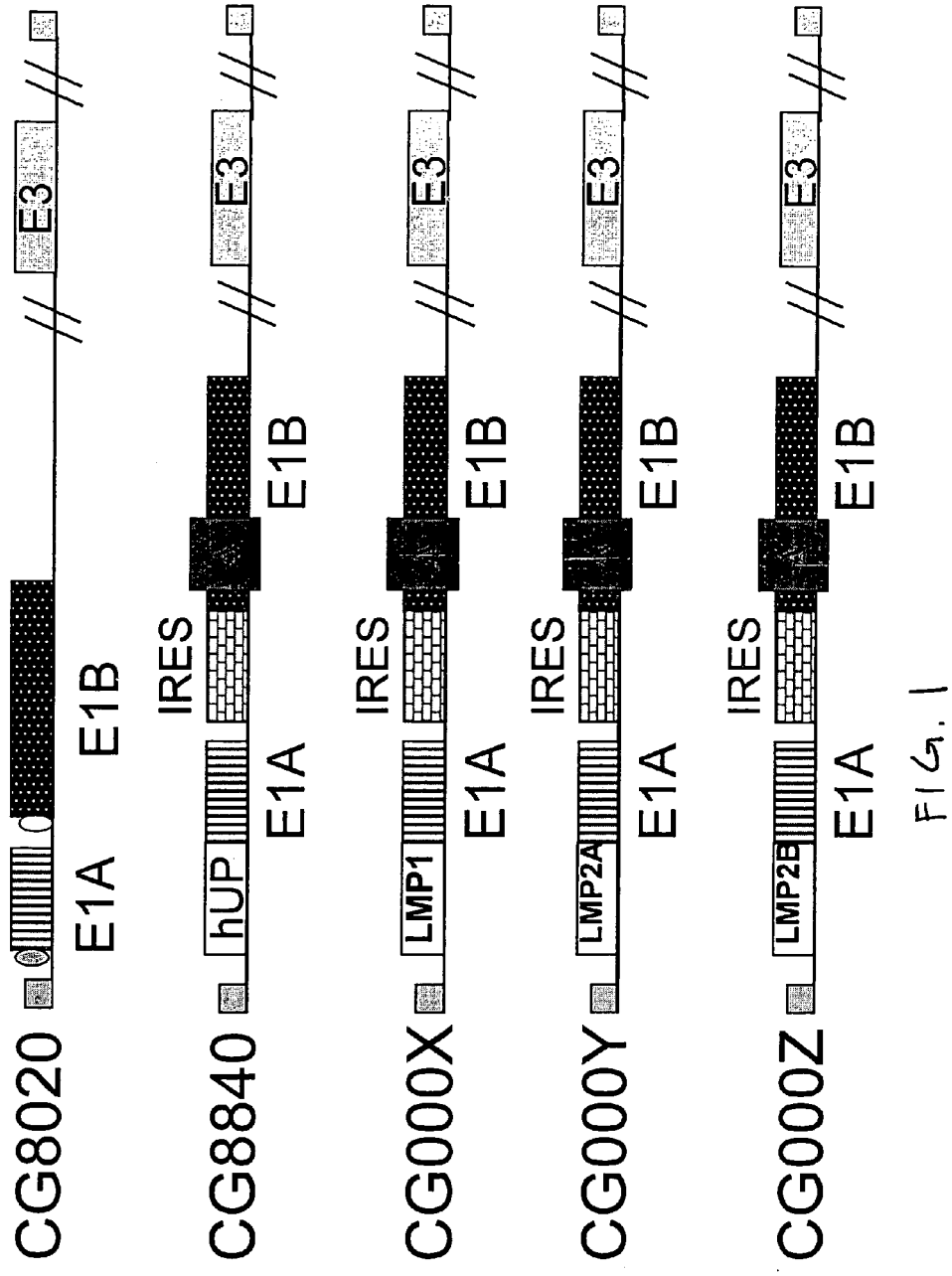
FIG. 1 depicts schematics of EBV-specific adenovirus vectors.

The EBV-specific replication-competent adenovirus vectors of the invention comprise an adenovirus gene essential for replication, preferably an early gene, under the transcriptional control of an EBV-specific transcriptional regulatory element (TRE). By providing one or more EBV-specific TREs, the adenovirus vectors effect selective replication and corresponding cytotoxicity in cancer cells associated with EBV. The EBV-specific TRE may comprise one or more regulatory sequences, e.g. enhancers, promoters, transcription factor binding sites and the like, which may be derived from the same or different genes. The adenovirus vectors may comprise co-transcribed first and second genes under control of a EBV-specific TRE, wherein the second gene may be under translational control of an internal ribosome entry site (IRES). In some cases, the adenovirus vectors comprise more than two co-transcribed genes under control of an EBV-specific TRE, wherein one or more genes is under translational control of an internal ribosome entry site (IRES). The adenovirus vectors of the invention may or may not comprise the adenoviral E3 gene, an E3 sequence, or a portion thereof. The adenovirus vectors may comprise genes under control of an EBV-specific TRE and one or more additional genes under control of a non-EBV TRE, that may or may not be cell type-specific.

In another aspect, methods are provided for conferring selective cytotoxicity in target cancer cells associated with EBV, comprising contacting the cells with an adenovirus vector of the invention, whereby the vector enters the cell and propagates virus. The replication of virus in such cells, as compared to non-tumor cells, or to normal, i.e. non-transformed cells, is usually about 10 fold greater, and may be about 100 fold greater, and in some instances is as much as about 1000 fold or more greater. Non-transformed cells include B cells that may carry latent EBV.

The administration of adenovirus may be combined with additional treatment(s) appropriate to the particular disease, e.g. chemotherapy, surgery, radiation therapy or immunotherapy. In some embodiments, this treatment suppresses tumor growth, e.g. by killing tumor cells. In other embodiments, the size and/or extent of a tumor is reduced, or its development delayed. Cytotoxicity is a term well understood in the art and refers to a state in which a cell's usual biochemical or biological activities are compromised (i.e., inhibited), including cell death and/or cytolysis. These activities include, but are not limited to, metabolism; cellular replication; DNA replication; transcription; translation; uptake of molecules. Assays known in the art as indicators of cytotoxicity, include dye exclusion, $^3$H-thymidine uptake, and plaque assays.

Individuals suitable for treatment by these methods include individuals who have or are suspected of having EBV-associated cancer, including individuals in the early or late stages of disease, as well as individuals who have previously been treated (e.g., are in the adjuvant setting). Other individuals suitable for the methods described herein are those who are considered at high risk for developing EBV-associated disease, such as those who are immunosuppressed, infected with HIV-1, etc. Treatment regimes include both the eradication of tumors or other forms of the disease as well as palliation of the disease. The presence of tumors and the suitability of the individual for treatment using the methods described herein may be determined by any of the techniques known in the art, including diagnostic methods such as imaging techniques, analysis of serum tumor markers, and biopsy.

In one aspect, the EBV specific TRE is derived from the sequence upstream of the translational start codon for the LMP1 (SEQ ID NO:1), LMP2A (SEQ ID NO:2) or LMP2B gene. Alternatively, the Cp promoter (SEQ ID NO:3), and/or the FR enhancer (SEQ ID NO:4) may be used.

The LMP1 mRNA is the most abundant EBV mRNA in latent infection. The LMP1 regulatory sequence is defined as comprising the region of nucleotides 169,474 to 170650 of B95-8 EBV DNA, which corresponds to the region upstream of LMP1 (using the published genome sequence, Genbank accession number NC_001345, as a reference); or a transcriptionally active fragment thereof. This region contains two distinct promoters, termed "ED-L1"; and "L1-TR" (which may also be referred to as ED-L1E). ED-L1 directed transcripts are generally found following initial infection, and in lymphoblastoid cells. L1-TR directed transcripts are found in EBV associated epithelial cells, nasopharyngeal carcinoma and Hodgkin's disease tissues. Both promoters respond to activation of JAK-STAT signaling, or the presence of IL-6. For the purposes of the present invention, as referred to herein an LMP1 promoter may comprise the complete regulatory region, or may comprise the regulatory sequences specific to the ED-L1 promoter; to the L1-TR promoter; or a combination thereof. Included as regulatory sequences are SP1 and STAT-binding sequences, as set forth below, TATA boxes, etc.

The ED-L1 promoter (TATA box) is found at position 169,546, having the sequence (complementary strand) TACATAA. The mRNA is reported to span from position 169,207 to 169,474, of which the coding sequence extends from position 169,386. The ED-L1 promoter contains a single STAT-binding site (TTTCCCGAA) located at position 169,634-169,643, and may comprise four additional potential Sp1-binding elements.

The L1-TR promoter comprises a transcription initiation site at nucleotide 170,099. The L1-TR promoter region does not contain TATA or CAAT box sequence elements, but includes GC boxes, which regulate transcription by binding of the Sp1 transcription factor. The 17-bp GC box region (GAGGGGGCGTGGCCTTC) is found at 170,130 to 170,147. A STAT binding region (TTCCTGGAA) is present at position 170,115 to 170,123.

The ED-L1 promoter (TATA box) is found at position 169,546, having the sequence (complementary strand) TACATAA (presented as the sequence complementary to nucleotides 64 to 70 of SEQ ID NO:1). The mRNA is reported to span from position 169,207 to 169,474, of which the coding sequence extends from position 169,386. The ED-L1 promoter contains a single STAT-binding site (TTTCCCGAA) located at position 169,634-169,643, (presented as the sequence complementary to nucleotides 158 to 167 of SEQ ID NO:1). and may comprise four additional potential Sp1-binding elements.

The L1-TR promoter comprises a transcription initiation site at nucleotide 1703099. The L1-TR promoter region does not contain TATA or CAAT box sequence elements, but includes GC boxes, which regulate transcription by binding of the Sp1 transcription factor. The 17-bp GC box region is found at 170,130 to 170,147 of B95-8 EBV DNA. A STAT binding region is present at position 170,115 to 170,123.

EBNA-LP is encoded by the leader of each of the EBNA mRNAs and encodes a protein of variable size depending on the number of repeats contained by a particular EBV isolate. LMP1 expression induces many of the changes associated with EBV infection and activation of primary B lymphocytes including cell clumping, increased cell surface expression of CD23, CD39, CD40, CD44, decreased expression of CD10, and increased expression of the cell adhesion molecules CD11a (LFA1), CD54 (ICAM1), and CD58 (LFA3). LMP1 has also been shown to protect B-lymphocytes from apoptosis via the induction of the anti-apoptotic proteins, Bcl-2, Mcl-1, and A20. LMP1 expression also affects the growth of epithelial cells, inducing epidermal hyperplasia when expressed in the skin of transgenic mice. In monolayer keratinocyte cultures, LMP1 alters cell morphology and cytokeratin expression, and inhibits cell differentiation of immortalised epithelial cells in raft cultures.

The LMP2 gene encodes two distinct proteins, LMP2A and LMP2B. The structures of LMP2A and LMP2B are similar; both have 12 transmembrane domains and a 27 amino acid cytoplasmic C-terminus, in addition LMP2A has a 119 amino acid cytoplasmic amino terminal domain. LMP2A aggregates in patches within the plasma membrane of latently infected B lymphocytes. The consistent expression of LMP2A in HD and NPC suggests an important function for this protein in oncogenesis.

The Cp promoter extends from position 10257 to 11479 of the EBV genome (ref: Fuentes-Panana et al, J. Virol., (1999) 73, 826-833 and V01555). The transcription start site is located at position 11334. EBNA2 is expressed from the viral C promoter (Cp) and regulates its own expression by activating Cp and EBNA2 expression; EBV controls the pattern of latent protein expression and the type of latency established.

The oriP FR (family of repeats) enhancer is the enhancer for the LMP promoter. It is an EBNA-1 dependent transcriptional enhancer. Located in oriP, the enhancer can increase the expression of a tagged viral oncogene encoding the latent membrane protein (LMP) up to 200 fold in normal EBV positive cells, see Reisman et al, (1985) Mol. Cell. Biol, 5, 1822-1832; and Genbank accession number V10555, DNA position 7421-8042 of EBV genome.

The various methods of the invention will be described below. Although particular methods of tumor suppression are exemplified in the discussion below, it is understood that any of a number of alternative methods, including those described above are equally applicable and suitable for use in practicing the invention. It will also be understood that an evaluation of the vectors and methods of the invention may be carried out using procedures standard in the art, including the diagnostic and assessment methods described above.

The practice of the present invention will employ, unless otherwise indicated, conventional techniques of molecular biology (including recombinant techniques), microbiology, cell biology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

For techniques related to adenovirus, see, inter alia, Felgner and Ringold (1989) *Nature* 337:387-388; Berkner and Sharp (1983) *Nucl. Acids Res.* 11:6003-6020; Graham (1984) *EMBO J.* 3:2917-2922; Bett et al. (1993) *J. Virology* 67:5911-5921; Bett et al. (1994) *Proc. Natl. Acad. Sci. USA* 91:8802-8806.

DEFINITIONS

Unless otherwise indicated, all terms used herein have the same meaning as they would to one skilled in the art and the practice of the present invention will employ, conventional techniques of microbiology and recombinant DNA technology, which are within the knowledge of those of skill of the art.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

EBV-associated tumors include a variety of lymphoid and epithelial cell derived tumors, e.g. lymphoproliferative disease, nasopharyngeal cancer, Hodgkin's Disease, Burkitt's lymphoma, and the like. Confirmation that a tumor is EBV-associated may utilize methods known in the art for determining the presence of the viral genome, mRNA or the encoded protein products; specific examples of expression products associated with a cancer are noted below. Methods of detecting the presence of a specific nucleic acid or polypeptide are well known in the art, e.g. southern blotting, quantitative PCR, in situ hybridization, ELISA, immunohistochemistry, and the like. There are different patterns of EBV gene expression during latency, which are also found in EBV-associated tumors. Latency III (Lat III) is observed in EBV transformed cell lines. Lat I is characterized by restricted viral gene expression involving only EBNA1, EBERs and the BARTs and is observable in EBV-associated BL. Lat II is seen in EBV-positive UNPC, HD and in some T-cell lymphomas where, in addition to EBNA1, EBERs and the BARTs, LMP1 and LMP2 are also expressed. In Lat I and Lat II, EBNA1 is expressed from an alternative promoter, now known as Qp.

Lymphoproliferative disease frequently develops in various immunosuppressive states. The prototypic EBV-induced lymphoproliferative disorder arises as a result of the iatrogenic immunosuppression of transplant patients, although similar disorders occur in some of the inherited immunodeficiencies and in patients with AIDS. The lymphoproliferations that arise following iatrogenic immunosuppression for transplant surgery are virtually always B cell in origin and are collectively known as post-transplant lymphoproliferative disorders (PTLDs). They represent a family of lesions ranging from spontaneously regressing a typical polyclonal B cell proliferations to aggressive non-Hodgkin's lymphomas (NHLs). Most lymphoproliferations that arise following solid organ grafts are of host cell origin, whereas those that occur after bone marrow transplant are often derived from donor cells. Most tumors generally present as multifocal lesions in extranodal locations such as the gastrointestinal tract or in the allograft organ itself. The incidence and clinical presentation of PTLD varies with the organ transplanted, the duration of immunosuppression and the dosage and number of agents used.

The majority of EBV-positive PTLD cases exhibit an unrestricted pattern of viral gene expression (Lat III) and are likely to be primarily driven by EBV. However, PTLD lesions can also present with patterns of expression similar to that seen in EBV-associated BL (Lat I) or EBV-associated HD and UNPC (Lat II). In many cases of EBV-positive PTLD the donor organ itself may be the source of EBV infection.

Burkitt's lymphoma (BL) is found at an annual incidence of approximately 5-10 cases per 100,000 children in areas restricted to equatorial Africa and Papua New Guinea. By contrast, sporadic cases of BL occur world-wide but at a much lower frequency. The endemic and sporadic forms of BL also differ in their association with EBV. Virtually every BL tumor found in the high-incidence regions is EBV positive, and about 15% of sporadic BL tumors carry the virus. Both endemic and sporadic BL are characterized by chromosome translocations involving chromosome 8 and either chromosome 14, 2, or 22. The most common translocation is the reciprocal t(8;14), which is present in approximately 80% of cases and results in MYC coding sequences being translocated to the Ig heavy chain constant region. EBNA1 is the only EBV protein consistently observed in EBV-positive BL tumors, although some reports have documented expression of LMP1 and EBNA2 in small numbers of cells. BL cells exhibit high level expression of CD10 and CD77.

Hodgkin's disease (HD). The presence of EBV DNA in HD tissue specimens has been demonstrated by in situ hybridization. EBV rates in HD tumors from North America and Europe have been shown to vary between 20-50%, whereas much higher rates are observed in underdeveloped countries such as Peru and Kenya. In most cases, type-1 EBV has been detected in HD tissues, although type-2 virus sequences are found in a lower proportion of cases and seem to be related to a clinical setting of immunodeficiency. Immunohistochemical assays and transcriptional analysis on fresh biopsies has demonstrated that the malignant Hodgkin/Reed-Sternberg (HRS) cells of EBV-positive cases express high levels of LMP1 in the absence of EBNA2 expression (Lat II pattern). EBV is preferentially associated with the mixed cellularity form of HD, irrespective of the precise lineage markers expressed on the HRS cells. HD in older patients (>55 years of age) and in children, especially boys under 10 years, has been shown to be more likely to be EBV-associated than HD in young adults. LMP1 is highly expressed in EBV-infected HRS cells.

T cell lymphomas. EBV has been linked to a proportion of peripheral T cell non-Hodgkin's lymphomas arising in patients without overt pre-existing immunodeficiency. A very high incidence of EBV genomes has also been reported in sinonasal T-NHLs occurring in Japanese, Chinese, Peruvian, European and United States patients. Sinonasal T-NHLs display peculiar phenotypic and genotypic features, including the frequent absence of T cell antigens, expression of NK cell markers and the absence of T cell receptor gene rearrangements. Frequently the virus is detected in only a fraction (5-50%) of the tumor cells, implying that EBV infection might have occurred subsequent to tumor development. Most EBV-associated T-NHLs are extranodal and have a cytotoxic phenotype.

Nasopharyngeal carcinoma. EBV DNA and the EBNA complex have been found in the tumor cells of undifferentiated nasopharyngeal carcinomas (UNPC) using in situ hybridisation and the anti-complement immunofluorescence (ACIF) assay. UNPCs are invariably EBV-positive regardless of geographical origin. EBNA1 and the EBERs are expressed in all EBV-positive cases and LMP1 is present in up to approximately 65% of cases. However, antibodies against structural viral proteins are frequently detectable in UNPC patient sera. In particular, patients with UNPC have elevated IgA antibody titres to the VCA, EA and MA complexes.

Other carcinomas. Carcinomas with similar features to UNPC may occur at other sites such as the thymus, tonsils, lungs, stomach, skin or uterine cervix, and are often referred to as undifferentiated carcinomas of nasopharyngeal type (UCNT). UCNTs of the stomach are consistently EBV-positive. EBV has been demonstrated in thymic epithelial tumors from Chinese patients. Salivary gland UCNTs are EBV-associated in Greenland Eskimos and Chinese, and several case reports have demonstrated the absence of EBV from UCNTs arising in the uterine cervix and breast. EBV is also found in a small proportion of typical gastric adenocarcinomas of either diffuse or intestinal type. Immunohistochemical studies of virus-associated gastric carcinomas (including both UCNTs and adenocarcinomas) have shown a restricted pattern of expression limited to the EBERs, EBNA1 and BZLF1, but not LMP1 or the other EBNAs.

EBV-associated breast cancer and hepatocellular carcinoma. The detection of EBV in a proportion of classical breast tumors by PCR, immunohistochemistry for EBNA1 protein, and Southern blotting has been reported. However, EBER expression was not detectable by in situ hybridisation. EBV was also detected more frequently in breast tumors that were hormone-receptor negative and of high histological grade. EBV has also been reported in a series of hepatocellular carcinomas (HCC), in the absence of EBER expression. Western blotting and reverse transcription-polymerase chain reaction also demonstrated expression of EBNA1 and the BamHI A transcripts.

As used herein, "suppressing tumor growth" refers to reducing the rate of growth of a tumor, halting tumor growth completely, causing a regression in the size of an existing tumor, eradicating an existing tumor and/or preventing the occurrence of additional tumors upon treatment with the compositions, k its or methods of the present invention. "Suppressing" tumor growth indicates a growth state that is curtailed when compared to growth without contact with, i.e., transfection by, an adenoviral vector combined with administration of chemotherapeutic agents and radiation as described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

"Delaying development" of a tumor means to defer, hinder, slow, retard, stabilize, and/or postpone development of the disease. This delay can be of varying lengths of time, depending on the history of the disease and/or individual being treated.

As used herein, a "transcription response element" or "transcriptional regulatory element", or "TRE" is a polynucleotide sequence, preferably a DNA sequence, comprising one or more enhancer(s) and/or promoter(s) and/or promoter elements such as a transcriptional regulatory protein response sequence or sequences, which increases transcription of an operably linked polynucleotide sequence in a host cell that allows that TRE to function. An "EBV-specific transcriptional response element" preferentially directs gene expression in EBV-associated cancer cells. "Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

By "transcriptional activation" or an "increase in transcription," it is intended that transcription is increased above basal levels in a normal, i.e. non-transformed cell by at least about 2 fold, preferably at least about 5 fold, preferably at least about 10 fold, more preferably at least about 20 fold, more preferably at least about 50 fold, more preferably at least about 100 fold, more preferably at least about 200 fold, even more preferably at least about 400 fold to about 500 fold, even more preferably at least about 1000 fold. Basal levels are generally the level of activity (if any) in a non-target cell (i.e., a cell type not associated with EBV), or the level of activity (if any) of a reporter construct lacking an EBV-specific TRE as tested in a target cell line. When the TRE controls a gene necessary for viral replication, the replication of virus is significantly higher in the target cells, as compared to a control cell, usually at least about 2-fold higher, preferably, at least about 5-fold higher, more preferably, at least about 10-fold higher, still more preferably at least about 50-fold higher, even more preferably at least about 100-fold higher, still more preferably at least about 400- to 500-fold higher, still more preferably at least about 1000-fold higher, most preferably at least about $1 \times 10^6$ higher. Most preferably, the adenovirus replicates solely in the target cells (that is, does not replicate or replicates at a very low levels in non-target cells).

Activity of a TRE can be determined, for example, as follows. A TRE polynucleotide sequence or set of such sequences can be generated using methods known in the art, such as chemical synthesis, site-directed mutagenesis, PCR, and/or recombinant methods. The sequence(s) to be tested can be inserted into a vector containing a promoter (if no promoter element is present in the TRE) and an appropriate reporter gene encoding a reporter protein, including, but not limited to, chloramphenicol acetyl transferase (CAT), β-galactosidase (encoded by the lacZ gene), luciferase (encoded by the luc gene), alkaline phosphatase (AP), green fluorescent protein (GFP), and horseradish peroxidase (HRP). Such vectors and assays are readily available, from, inter alia, commercial sources. Plasmids thus constructed are transfected into a suitable host cell to test for expression of the reporter gene as controlled by the putative TRE using transfection methods known in the art, such as calcium phosphate precipitation, electroporation, liposomes, DEAE dextran-mediated transfer, particle bombardment or direct injection. TRE activity is measured by detection and/or quantitation of reporter gene-derived mRNA and/or protein. Reporter protein product can be detected directly (e.g., immunochemically) or through its enzymatic activity, if any, using an appropriate substrate. Generally, to determine cell specific activity of a TRE, a TRE-reporter gene construct is introduced into a variety of cell types. The amount of TRE activity is determined in each cell type and compared to that of a reporter gene construct lacking the TRE. A TRE is determined to be cell-specific if it is preferentially functional in one cell type, compared to a different type of cell.

An EBV specific TRE comprises an EBV-specific enhancer and/or promoter, including the LMP1 and LMP2 promoters; the Cp promoter, and the FR enhancer. Preferred promoter and enhancer elements and transcription factor binding sequences include one or both of the sequences set forth in SEQ ID NO:1-4. This region of DNA contains the viral promoter elements that direct expression of the linked gene.

An EBV-specific TRE can also comprise multimers. For example, an EBV-specific TRE can comprise a tandem series of at least two, at least three, at least four, or at least five promoter fragments. Alternatively, an EBV-specific TRE could have one or more promoter regions along with one or more enhancer regions. These multimers may also contain heterologous promoter and/or enhancer sequences and/or transcription factor binding sites.

The promoter enhancer and/or transcription factor binding site components of an EBV-specific TRE may be in any orientation and/or distance from the coding sequence of interest, as long as the desired target cell-specific transcriptional activity is obtained. Transcriptional activation can be measured in a number of ways known in the art, but is generally measured by detection and/or quantitation of mRNA or the protein product of the coding sequence under control of (i.e., operably linked to) the EBV-specific TRE. As discussed herein, an EBV-specific TRE can be of varying lengths, and of varying sequence composition.

The term "composite TRE" refers to a TRE that comprises transcriptional regulatory elements that are not naturally found together, usually providing a non-native combination of promoters and enhancer, for example, a heterologous combination of promoter and enhancer and/or transcription factor binding sites; a combination of human and mouse promoter and enhancer; two or more enhancers in combination with a promoter; multimers of the foregoing; and the like. At least one of the promoter, enhancer or and/or transcription factor binding site elements will be EBV specific, for example an LMP promoter in combination with an enhancer. In other embodiments, two or more of the elements will provide EBV specificity.

As is known in the art, the activity of TREs can be inducible. Inducible TREs generally exhibit low activity in the absence of inducer, and are up-regulated in the presence of inducer. Inducers include, for example, nucleic acids, polypeptides, small molecules, organic compounds and/or environmental conditions such as temperature, pressure or hypoxia. Inducible TREs may be preferred when expression is desired only at certain times or at certain locations, or when it is desirable to titrate the level of expression using an inducing agent.

A TRE for use in the present vectors may or may not comprise a silencer. The presence of a silencer (i.e., a negative regulatory element known in the art) can assist in shutting off transcription (and thus replication) in non-target cells. Thus, the presence of a silencer can confer enhanced cell-specific vector replication by more effectively preventing replication in non-target cells. Alternatively, the lack of a silencer may stimulate replication in target cells, thus conferring enhanced target cell-specificity.

A "functionally-preserved variant" of an EBV-specific TRE differs, usually in sequence, but still retains the biological activity, e.g., target cell-specific transcription activity of the corresponding native or parent EBV-specific TRE, although the degree of activation may be altered. The difference in sequence may arise from, for example, single base mutation(s), addition(s), deletion(s), and/or modification(s) of the bases. The difference can also arise from changes in the sugar(s), and/or linkage(s) between the bases of an EBV-specific TRE. For example, certain point mutations within sequences of TREs have been shown to decrease transcription factor binding and stimulation of transcription (see Blackwood, et al. (1998) *Science* 281:60-63, and Smith et al., (1997) *J. Biol. Chem.* 272:27493-27496). One of skill in the art would recognize that some alterations of bases in and around transcription factor binding sites are more likely to negatively affect stimulation of transcription and cell-specificity, while alterations in bases that are not involved in transcription factor binding are not as likely to have such effects. Certain mutations are also capable of increasing TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription. It will be appreciated that typically a "functionally-preserved variant" of an EBV-specific TRE will hybridize to the parent sequence under conditions of high stringency. Exemplary high stringency conditions include hybridization at about 65° C. in about 5×SSPE and washing at about 65° C. in about 0.1×SSPE (where 1×SSPE=0.15 sodium chloride, 0.010 M sodium phosphate, and 0.001 M disodium EDTA). Further examples of high stringency conditions are provided in: Maniatis, et al., MOLECULAR CLONING: A LABORATORY MANUAL, 2d Edition (1989); and Ausubel, F. M., et al., Eds., CURRENT ROTOCOLS IN MOLECULAR BIOLOGY, John Wiley & Sons, Inc., Copyright (c) 1987, 1988, 1989, 1990 by Current Protocols, both of which are hereby incorporated by reference.

In some instances, a "functionally-preserved variant" of an EBV-specific TRE is a fragment of a native or parent EBV-specific TRE. The term "fragment," when referring to an EBV-specific TRE, refers to a sequence that is the same as part of, but not all of, the nucleic acid sequence of a native or parental EBV-specific TRE. Such a fragment either exhibits essentially the same biological function or activity as the native or parental EBV-specific TRE; for example, a fragment which retains the target cell-specific transcription activity of the corresponding native or parent EBV-specific TRE, although the degree of activation may be altered.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene (Jackson et al. (1990) *Trends Biochem Sci* 15(12):477-83) and Jackson et al. (1995) *RNA* 1(10):985-1000). The present invention encompasses the use of any IRES element that is able to direct internal ribosome entry to the initiation codon of a cistron. "Under translational control of an IRES" as used herein means that translation is associated with the IRES and proceeds in a cap-independent manner. Examples of "IRES" known in the art include, but are not limited to IRES obtainable from picornavirus (Jackson et al., 1990, *Trends Biochem Sci* 15(12):477-483); and IRES obtainable from viral or cellular mRNA sources, such as for example, immunogloublin heavy-chain binding protein (BiP), the vascular endothelial growth factor (VEGF) (Huez et al. (1998) *Mol. Cell. Biol.* 18(11):6178-6190), the fibroblast growth factor 2, and insulin-like growth factor, the translational initiation factor eIF4G, yeast transcription factors T FIID and HAP4. IRES have also been reported in different viruses such as cardiovirus, rhinovirus, aphthovirus, HCV, Friend murine leukemia virus (FrMLV) and Moloney murine leukemia virus (MoMLV). As used herein, the term "IRES" encompasses functional variations of IRES sequences as long as the variation is able to promote direct internal ribosome entry to the initiation codon of a cistron. In preferred embodiments, the IRES is mammalian. In other embodiments, the IRES is viral or protozoan. In one illustrative embodiment disclosed herein, the IRES is obtainable from encephelomycarditis virus (ECMV) (commercially available from Novogen, Duke et al. (1992) *J. Virol* 66(3): 1602-1609). In another illustrative embodiment disclosed herein, the IRES is from VEGF. In some embodiments, an adenovirus vector comprising an IRES and a target cell-specific TRE exhibits greater specificity for the target cell than an adenovirus vector comprising a target cell-specific TRE and lacking an IRES.

In other embodiments, specificity is conferred by preferential transcription and/or translation of the first and second genes due to the presence of a target cell specific TRE. In other embodiments, specificity is conferred by preferential replication of the adenovirus vectors in target cells due to the target cell-specific TRE driving transcription of a gene essential for replication.

An "E3 region" (used interchangeably with "E3") is a term well understood in the art and means the region of the adenoviral genome that encodes the E3 gene products. Generally, the E3 region is located between about nucleotides 28583 and 30470 of the adenoviral genome. The E3 region has been described in various publications, including, for example, Wold et al. (1995) *Curr. Topics Microbiol. Immunol.* 199:237-274. A "portion" of the E3 region means less than the entire E3 region, and as such includes polynucleotide deletions as well as polynucleotides encoding one or more polypeptide products of the E3 region.

A "multicistronic transcript" refers to an mRNA molecule that contains more than one protein coding region, or cistron. A mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of a mRNA molecule.

As used herein, "co-transcribed" means that two (or more) coding regions of polynucleotides are under transcriptional control of a single transcriptional control element.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

An "EBV-specific adenovirus vector" or "EBV-specific adenoviral vector" (used interchangeably) of the invention is a polynucleotide construct, which is replication competent, exhibits preferential replication in EBV-associated cancer cells and contains a tissue-specific transcriptional regulatory sequence linked to an adenoviral gene. In some embodiments, an EBV-specific adenoviral vector of the invention includes a therapeutic gene sequence, e.g., a cytokine gene sequence. Exemplary EBV-specific adenoviral vectors of the invention include, but are not limited to, DNA, DNA encapsulated in an adenovirus coat, adenoviral DNA packaged in another viral or viral-like form (such as herpes simplex, and AAV), adenoviral DNA encapsulated in liposomes, adenoviral DNA complexed with polylysine, adenoviral DNA complexed with synthetic polycationic molecules, conjugated with transferrin, or complexed with compounds such as PEG to immunologically "mask" the antigenicity and/or increase half-life, or conjugated to a nonviral protein.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. Preferably, an adenoviral polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18. A preferred alignment program is ALIGN Plus (Scientific and Educational Software, Pennsylvania), preferably using default parameters, which are as follows: mismatch=2; open gap=0; extend gap=2.

In the context of adenovirus, a "heterologous polynucleotide" or "heterologous gene" or "transgene" is any polynucleotide or gene that is not present in wild-type adenovirus. Preferably, the transgene will also not be expressed or present in the target cell prior to introduction by the adenovirus vector. Examples of preferred transgenes for inclusion in the adenovirus vectors of the invention, are provided below.

In the context of adenovirus, a "heterologous" promoter or enhancer is one which is not associated with or derived from an adenovirus gene.

In the context of a target cell-specific TRE, a "heterologous" promoter or enhancer is one which is derived from a gene other than the gene from which a particular target cell-specific TRE is derived.

In the context of adenovirus, an "endogenous" promoter, enhancer, or TRE is native to or derived from adenovirus.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a virus yield assay, burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

"Preferential replication" and "selective replication" may be used interchangeably and mean that an adenovirus replicates more in a target cell than in a non-target cell. Preferably, the adenovirus replicates at a significantly higher rate in target cells than non target cells; preferably, at least about 5-fold higher, more preferably, at least about 10-fold higher, still more preferably at least about 50-fold higher, even more preferably at least about 100-fold higher, still more preferably at least about 400- to 500-fold higher, still more preferably at least about 1000-fold higher, most preferably at least about $1 \times 10^6$ higher. Most preferably, the adenovirus replicates only in the target cells (that is, does not replicate at all or replicates at a very low level in non-target cells).

An "individual" is a vertebrate, preferably a mammal, more preferably a human. Mammals include, but are not limited to, farm animals, sport animals, rodents, primates, and pets. A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

As used herein, "cytotoxicity" is a term well understood in the art and refers to a state in which a cell's usual biochemical or biological activities are compromised (i.e., inhibited). These activities include, but are not limited to, metabolism; cellular replication; DNA replication; transcription; translation; uptake of molecules. "Cytotoxicity" includes cell death and/or cytolysis. Assays are known in the art which indicate cytotoxicity, such as dye exclusion, $^3$H-thymidine uptake, and plaque assays.

The term "selective cytotoxicity", as used herein, refers to the cytotoxicity conferred by an adenovirus vector of the invention on a cell which allows or induces a target cell-specific TRE to function (referred to herein as a "target cell") when compared to the cytotoxicity conferred by an adenoviral vector of the present invention on a cell which does not allow a target cell-specific TRE to function (a "non-target cell"). Such cytotoxicity may be measured, for example, by plaque assays, by reduction or stabilization in size of a tumor comprising target cells, or the reduction or stabilization of serum levels of a marker characteristic of the tumor cells, or a tissue-specific marker, e.g., a cancer marker.

Adenoviral Vectors

The EBV-specific adenoviral vectors described herein are replication-competent EBV-specific adenoviral vectors comprising an adenovirus gene, preferably a gene essential for replication under transcriptional control of an EBV-specific TRE. The vector may or may not include an E3 region. In other embodiments, an EBV-specific adenovirus vector is a replication competent EBV-specific vector comprising E1B, wherein E1B has a deletion of part or all of the 19-kDa region. In some embodiments the adenoviral gene essential for replication is an early gene, preferably E1A or E1B or both. In some embodiments, the EBV-specific adenovirus vector comprises co-transcribed first and second genes under transcriptional control of a heterologous, EBV-specific transcriptional regulatory element (TRE), wherein the second gene is under translational control of an internal ribosome entry site (IRES). The EBV-specific adenovirus vector may further comprise E3.

The E1B 19-kDa region refers to the genomic region of the a denovirus E1B gene encoding the E1B 19-kDa product. According to wild-type Ad5, the E1B 19-kDa region is a 261 bp region located between nucleotide 1714 and nucleotide 2244. The E1B 19-kDa region has been described in, for example, Rao et al., *Proc. Nat. Acad. Sci. USA*, 89:7742-7746. The present invention encompasses deletion of part or all of the E1B 19-kDa region as well as embodiments wherein the E1B 19-kDa region is mutated, as long as the deletion or mutation lessens or eliminates the inhibition of apoptosis associated with E1B-19 kDa.

The adenovirus vectors used in this invention replicate preferentially in EBV-associated cancer cells, in which there is active expression of EBV sequences. The replication preference is indicated by comparing the level of replication (i.e., titer) in such cells to the level of replication in non-EBV infected cells, normal or control cells. Comparison of the adenovirus titer of an EBV-associated cancer cell to the titer of a TRE inactive cell type provides a key indication that the overall replication preference is enhanced due to the replication in target cells as well as depressed replication in non-target cells. Runaway infection is prevented due to the cell-specific requirements for viral replication. Without wishing to be bound by any particular theory, production of adenovirus proteins can serve to activate and/or stimulate the immune system, either generally or specifically toward target cells producing adenoviral proteins which can be an important consideration in the cancer context, where individuals are often moderately to severely immunocompromised.

In one aspect of the present invention, the EBV-specific adenovirus vectors comprise an intergenic IRES element(s) which links the translation of two or more genes, thereby removing any potential for homologous recombination based on the presence of identical TREs in the vector. Adenovirus vectors comprising an IRES are stable and in some embodiments provide better specificity than vectors not containing an IRES. Another advantage of an adenovirus vector comprising an intergenic IRES is that the use of an IRES rather than a second TRE may provide additional space in the vector for an additional gene(s) such as a therapeutic gene. Accordingly, in one aspect of the invention, the EBV-specific viral vectors disclosed herein typically comprise at least one IRES within a multicistronic transcript, wherein production of the multicistronic transcript is regulated by a heterologous, target cell-specific TRE. F or EBV-specific a denovirus vectors comprising a second gene under control of an IRES, it is preferred that the endogenous promoter of the gene under translational control of an IRES be deleted so that the endogenous promoter does not interfere with transcription of the second gene. It is preferred that the second gene be in frame with the IRES if the IRES contains an initiation codon. If an initiation codon, such as ATG, is present in the IRES, it is preferred that the initiation codon of the second gene is removed and that the IRES and the second gene are in frame. Alternatively, if the IRES does not contain an initiation codon or if the initiation codon is removed from the IRES, the initiation codon of the second gene is used. In one embodiment, the a denovirus vectors comprise the adenovirus essential genes, E1A and E1B genes, under the transcriptional control of a heterologous EBV-specific TRE, and an IRES introduced between E1A and E1B. Thus, both E1A and E1B are under common transcriptional control, and translation of E1B coding region is obtained by virtue of the presence of the IRES. In one embodiment, E1A has its endogenous promoter deleted. In another embodiment, E1A has an endogenous enhancer deleted and in yet an additional embodiment, E1A has its endogenous promoter deleted and E1A enhancer deleted. In another embodiment, E1B has its endogenous promoter deleted. In yet further embodiments, E1B has a deletion of part or all of the 19-kDa region of E1B.

An EBV-specific adenovirus vector may further include an additional heterologous TRE which may or may not be operably linked to the same gene(s) as the target cell-specific TRE. For example a TRE (such as a cell type-specific or cell status-specific TRE) may be juxtaposed to a second type of target-cell-specific TRE. "Juxtaposed" means a target cell-specific TRE and a second TRE transcriptionally control the same gene. For these embodiments, the target cell-specific TRE and the second TRE may be in any of a number of configurations, including, but not limited to, (a) next to each other (i.e., abutting); (b) both 5' to the gene that is transcriptionally controlled (i.e., may have intervening sequences between them); (c) one TRE 5' and the other TRE 3' to the gene. An EBV-specific adenoviral vector of the invention may comprise one or more additional cancer-cell specific TREs. For example, a replication-competent EBV-specific adenovirus vector of the invention may comprise any of a number of cell type specific TREs, such as described in co-owned PCT/US2001/09042 (WO 01/72341), expressly incorporated by reference herein. In other exemplary embodiments, the EBV-specific adenoviral vector comprises a hypoxia responsive element (HRE) with a binding site for hypoxia inducible factor-1 or a cell cycle-specific TRE, e.g., derived from the E2F15' flanking region, as described in co-owned PCT/US1999/20718 (WO 00/15820), expressly incorporated by reference herein. In further exemplary embodiments, the EBV-specific adenoviral vector comprises a regulatory sequence of the H19 gene (Brannan et al., 1990, Molec. Cell. Biol. 10:28-36), or a regulatory sequence of the telomerase gene (Majumdar A S et al., Gene Ther 2001, 8(7):568-78), expressly incorporated by reference herein.

To enhance cytotoxicity to target cells, one or more transgenes having a cytotoxic effect may be present in the vector. Additionally, or alternatively, an adenovirus gene that contributes to cytotoxicity and/or cell death, such as the adenovirus death protein (ADP) gene, can be included in the vector, optionally under the selective transcriptional control of a heterologous TRE and optionally under the translational control of an IRES.

In some embodiments, an adenovirus vector of the invention comprises a transgene, which may confer a therapeutic effect, such as enhancing cytotoxicity so as to eliminate unwanted target cells. The transgene may be under the transcriptional control of an EBV TRE, e.g. an LMP TRE, which may comprise an LMP promoter. The transgene may be regulated independently of the adenovirus gene regulation, i.e. having separate promoters, which may the same or different, or may be coordinately regulated, i.e. having a single promoter in conjunction with an IRES. The therapeutic gene may be under transcriptional control of a cell type-specific TRE or a non-cell type specific TRE.

In this way, various genetic capabilities may be introduced into target cells, particularly cancer cells. For example, in certain instances, it may be desirable to enhance the degree and/or rate of cytotoxic activity, due to, for example, the relatively refractory nature or particular aggressiveness of the cancerous target cell. This could be accomplished by coupling the target cell-specific cytotoxic activity with cell-specific expression of, for example, HSV-tk and/or cytosine deaminase (cd). Cancer cells can be induced to be conditionally sensitive to the antiviral drug ganciclovir after transduction with HSV-tk. Ganciclovir is converted by HSV-tk into its triphosphate form by cellular enzymes and incorporated into the DNA of replicating mammalian cells leading to inhibition of DNA replication and cell death. Cytosine deaminase renders cells capable of metabolizing 5-fluorocytosine (5-FC) to the chemotherapeutic agent 5-fluorouracil (5-FU).

Other desirable transgenes that may be introduced via an adenovirus vector(s) include genes encoding cytotoxic proteins, such as the A chains of diphtheria toxin, ricin or abrin (Palmiter et al. (1987) *Cell* 50: 435; Maxwell et al. (1987) *Mol. Cell. Biol.* 7: 1576; Behringer et al. (1988) *Genes Dev.* 2: 453; Messing et al. (1992) *Neuron* 8: 507; Piatak et al. (1988) *J. Biol. Chem.* 263: 4937; Lamb et al. (1985) *Eur. J. Biochem.* 148: 265; Frankel et al. (1989) *Mol. Cell. Biol.* 9: 415), genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly; genes that encode an engineered cytoplasmic variant of a nuclease (e.g. RNase A) or protease (e.g. awsin, papain, proteinase K, carboxypeptidase, etc.), or encode the Fas gene, and the like.

Other therapeutic genes of interest include cytokines, antigens, transmembrane proteins, and the like, such as IL-1, -2, -6, -12, GM-CSF, G-CSF, M-CSF, IFN-α, -β, -χ, TNF-α, -β, TGF-α, -β, NGF, and the like.

Functionally preserved variants of TREs can be used in the vectors disclosed herein. Variant TREs retain function in the target cell but need not exhibit maximal function. In fact, maximal transcriptional activation activity of a TRE may not always be necessary to achieve a desired result, and the level of induction afforded by a fragment of a TRE may be sufficient for certain applications. For example, if used for treatment or palliation of a disease state, less-than-maximal responsiveness may be sufficient if, for example, the target cells are not especially virulent and/or the extent of disease is relatively confined.

As discussed herein, a TRE can be of varying lengths, and of varying sequence composition. The size of a heterologous TRE will be determined in part by the capacity of the viral vector, which in turn depends upon the contemplated form of the vector (see infra). Generally minimal sizes are preferred for TREs, as this provides potential room for insertion of other sequences which may be desirable, such as transgenes, and/or additional regulatory sequences. In a preferred embodiment, such an additional regulatory sequence is an IRES. However, if no additional sequences are contemplated, or if, for example, an adenoviral vector will be maintained and delivered free of any viral packaging constraints, larger TRE sequences can be used as long as the resultant adenoviral vector remains replication-competent.

To minimize non-specific replication, endogenous adenovirus TREs are preferably removed from the vector. Besides facilitating target cell-specific replication, removal of endogenous TREs also provides greater insert capacity in a vector, which may be of special concern if an adenoviral vector is to be packaged within a virus particle. Even more importantly, deletion of endogenous TREs prevents the possibility of a recombination event whereby a heterologous TRE is deleted and the endogenous TRE assumes transcriptional control of its respective adenovirus coding sequences. However, endogenous TREs can be maintained in the adenovirus vector(s), provided that sufficient cell-specific replication preference is preserved. These embodiments are constructed by inserting heterologous TREs between an endogenous TRE and a replication gene coding segment. Requisite EBV-specific replication preference is determined by conducting assays that compare replication of the adenovirus vector in a cell that allows function of the heterologous TREs with replication in a cell that does not.

The EBV-specific adenovirus vectors of this invention can be prepared using recombinant techniques that are standard in the art. Generally, an EBV-specific TRE is inserted 5' to the adenoviral gene of interest, preferably an adenoviral replication gene, more preferably one or more early replication genes (although late gene(s) can be used). An EBV-specific TRE can be prepared using oligonucleotide synthesis (if the sequence is known) or recombinant methods (such as PCR and/or restriction enzymes). Convenient restriction sites, either in the natural adeno-DNA sequence or introduced by methods such as PCR or site-directed mutagenesis, provide an insertion site for an EBV-specific TRE. Accordingly, convenient restriction sites for annealing (i.e., inserting) an EBV-specific TRE can be engineered onto the 5' and 3' ends of a UP-TRE using standard recombinant methods, such as PCR.

Adenoviral vectors containing all replication-essential elements, with the desired elements (e.g., E1A) under control of a EBV-specific TRE, are conveniently prepared by homologous recombination or in vitro ligation of two plasmids, one providing the left-hand portion of adenovirus and the other plasmid providing the right-hand region, one or more of which contains at least one adenovirus gene under control of an EBV-specific TRE. If homologous recombination is used, the two plasmids should share at least about 500 bp of sequence overlap. Each plasmid, as desired, may be independently manipulated, followed by cotransfection in a competent host, providing complementing genes as appropriate, or the appropriate transcription factors for initiation of transcription from an EBV-specific TRE for propagation of the adenovirus. Plasmids are generally introduced into a suitable host cell such as 293 cells using appropriate means of transduction, such as cationic liposomes. Alternatively, in vitro ligation of the right and left-hand portions of the adenovirus genome can also be used to construct recombinant adenovirus derivative containing all the replication-essential portions of adenovirus genome. Berkner et al. (1983) *Nucleic Acid Research* 11: 6003-6020; Bridge et al. (1989) *J. Virol.* 63: 631-638.

For convenience, plasmids are available that provide the necessary portions of adenovirus. Plasmid pXC.1 (McKinnon (1982) *Gene* 19:33-42) contains the wild-type left-hand end of Ad5. pBHG10 (Bett et al. (1994); Microbix Biosystems Inc., Toronto) provides the right-hand end of Ad5, with a deletion in E3. The deletion in E3 provides room in the virus to insert a 3 kb TRE without deleting the endogenous enhancer/promoter. The gene for E3 is located on the opposite strand from E4 (r-strand). pBHG11 provides an even larger E3 deletion (an additional 0.3 kb is deleted). Bett et al. (1994). Alternatively, the use of pBHGE3 (Microbix Biosystems, Inc.) provides the right hand end of Ad5, with a full-length of E3.

For manipulation of the early genes, the transcription start site of Ad5 E1A is at 498 and the ATG start site of the E1A coding segment is at 560 in the virus genome. This region can be used for insertion of an EBV-specific TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a nucleotide sequence change resulting in a unique restriction site, one can provide for insertion of a EBV-specific TRE at that site.

A similar strategy may also be used for insertion of an EBV-specific TRE element to regulate E1B. The E1B promoter of Ad5 consists of a single high-affinity recognition site for Spl and a TATA box. This region extends from Ad5 nt 1636 to 1701. By insertion of a TRE in this region, one can provide for cell-specific transcription of the E1B gene. By employing the left-hand region modified with the cell-specific response element regulating E1A, as the template for introducing an EBV-specific TRE to regulate E1B, the resulting adenovirus vector will be dependent upon the cell-specific transcription factors for expression of both E1A and E1B. In some embodiments, part or all of the 19-kDa region of E1B is deleted.

Similarly, an EBV-specific TRE can be inserted upstream of the E2 gene to make its expression cell-specific. The E2 early promoter, mapping in Ad5 from 27050-27150, consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan et al., *Curr. Topics in Micro. and Immunol.* (1995) 199(part 3):177-194.

The E2 late promoter overlaps with the coding sequences of a gene encoded by the counterstrand and is therefore not amenable for genetic manipulation. However, the E2 early promoter overlaps only for a few base pairs with sequences coding for a 33 kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor binding sites E2F and ATF. Therefore, insertion of an EBV-specific TRE having SpeI ends into the SpeI site in the 1-strand would disrupt the endogenous E2 early promoter of Ad5 and should allow cell-restricted expression of E2 transcripts.

For E4, one must use the right hand portion of the adenovirus genome. The E4 transcription start site is predominantly at about nt 35605, the TATA box at about nt 35631 and the first AUG/CUG of ORF I is at about nt 35532. Virtanen et al. (1984) *J. Virol.* 51: 822-831. Using any of the above strategies for the other genes, a UP-TRE may be introduced upstream from the transcription start site. For the construction of full-length adenovirus with a EBV-specific TRE inserted in the E4 region, the co-transfection and homologous recombination are performed in W162 cells (Weinberg et al. (1983) *Proc. Natl. Acad. Sci.* 80:5383-5386) which provide E4 proteins in trans to complement defects in synthesis of these proteins.

Adenoviral constructs containing an E3 region can be generated wherein homologous recombination between an E3-containing adenoviral plasmid, for example, BHGE3 (Microbix Biosystems Inc., Toronto) and a non-E3-containing adenoviral plasmid, is carried out.

Alternatively, an adenoviral vector comprising an E3 region can be introduced into cells, for example 293 cells, along with an adenoviral construct or an adenoviral plasmid construct, where they can undergo homologous recombination to yield adenovirus containing an E3 region. In this case, the E3-containing adenoviral vector and the adenoviral construct or plasmid construct contain complementary regions of adenovirus, for example, one contains the left-hand and the other contains the right-hand region, with sufficient sequence overlap as to allow homologous recombination.

Alternatively, an E3-containing adenoviral vector of the invention can be constructed using other conventional methods including standard recombinant methods (e.g., using restriction nucleases and/or PCR), chemical synthesis, or a combination of any of these. Further, deletions of portions of the E3 region can be created using standard techniques of molecular biology.

Insertion of an IRES into a vector is accomplished by methods and techniques that are known in the art and described herein supra, including but not limited to, restriction enzyme digestion, ligation, and PCR. A DNA copy of an IRES can be obtained by chemical synthesis, or by making a cDNA copy of, for example, a picornavirus IRES. See, for example, Duke et al. (1995) *J. Virol.* 66(3):1602-9) for a description of the EMCV IRES and Huez et al. (1998), *Mol. Cell. Biol.* 18(11):6178-90) for a description of the VEGF IRES. The internal translation initiation sequence is inserted into a vector genome at a site such that it lies upstream of a 5'-distal coding region in a multicistronic mRNA. For example, in a preferred embodiment of an adenovirus vector in which production of a bicistronic E1A-E1B mRNA is under the control of an EBV-specific TRE, the E1B promoter is deleted or inactivated, and an IRES sequence is placed between E1A and E1B. In other embodiments, part or all of the 19-kDa region of E1B is deleted. IRES sequences of cardioviruses and certain aphthoviruses contain an AUG codon at the 3' end of the IRES that serves as both a ribosome entry site and as a translation initiation site. Accordingly, this type of IRES is introduced into a vector so as to replace the translation initiation codon of the protein whose translation it regulates. However, in an IRES of the entero/rhinovirus class, the AUG at the 3' end of the IRES is used for ribosome entry only, and translation is initiated at the next downstream AUG codon. Accordingly, if an entero/rhinovirus IRES is used in a vector for translational regulation of a downstream coding region, the AUG (or other translation initiation codon) of the downstream gene is retained in the vector construct.

Methods of packaging polynucleotides into adenovirus particles are known in the art and are also described in co-owned PCT/US98/04080.

Therapeutic Methods

An effective amount of the adenovirus vector is administered to a patient as a composition in a pharmaceutically acceptable excipient (and may or may not be in the same compositions), including, but not limited to, saline solutions, suitable buffers, preservatives, stabilizers, and may be administered in conjunction with suitable agents such as antiemetics. An effective amount is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state. Some individuals are refractory to these treatments, and it is understood that the methods encompass administration to these individuals. The amount to be given will be determined by the condition of the individual, the extent of disease, the route of administration, how many doses will be administered, and the desired objective.

Delivery of adenoviral vectors is generally accomplished by either site-specific injection or intravenous injection. Site-specific injections of vector may include, for example, injections into nasopharyngeal lesions, as well as intraperitoneal, intrapleural, intrathecal, intra-arterial, intra-tumor injections or topical application. These methods are easily accommodated in treatments using the combination of adenoviral vectors and chemotherapeutic agents.

The adenoviral vectors may be delivered to the target cell in a variety of ways, including, but not limited to, liposomes, general transfection methods that are well known in the art (such as calcium phosphate precipitation or electroporation), direct injection, and intravenous infusion. The means of delivery will depend in large part on the particular adenoviral vector (including its form) as well as the type and location of the target cells (i.e., whether the cells are in vitro or in vivo).

If used as a packaged adenovirus, a denovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 µg to about 1000 µg of an adenoviral vector can be administered. The adenoviral vector(s) may be administered one or more times, depending upon the intended use and the immune response potential of the host, and may also be administered as multiple, simultaneous injections. If an immune response is undesirable, the immune response may be diminished by employing a variety of immunosuppressants, or by employing a technique such as an immunoadsorption procedure (e.g., immunoapheresis) that removes adenovirus antibody from the blood, so as to permit repetitive administration, without a strong immune response. If packaged as another viral form, such as HSV, an amount to be administered is based on standard knowledge about that particular virus (which is readily obtainable from, for example, published literature) and can be determined empirically.

Embodiments of the present invention include methods for the administration of combinations of an EBV-specific adenoviral vector and a second anti-neoplastic therapy, which may include radiation, an anti-neoplastic agent, etc., to an individual with neoplasia, as detailed in co-owned U.S. application Ser. No. 09/814,357, expressly incorporated by reference herein. The chemotherapeutic agent and adenovirus may be administered simultaneously or sequentially, with various time intervals for sequential administration. In some embodiments, an effective amount of an adenoviral vector and an effective amount of at least one antineoplastic agent are combined with a suitable excipient and/or buffer solutions and administered simultaneously from the same solution by any of the methods listed herein or those known in the art. This may be applicable when the antineoplastic agent does not compromise the viability and/or activity of the adenoviral vector itself.

Where more than one antineoplastic agent is administered, the agents may be administered together in the same composition; sequentially in any order; or, alternatively, administered simultaneously in different compositions. If the agents are administered sequentially, administration may further comprise a time delay. Sequential administration may be in any order, and accordingly encompasses the administration of an effective amount of an adenoviral vector first, followed by the administration of an effective amount of the chemotherapeutic agent. The interval between administration of adenovirus and chemotherapeutic agent may be in terms of at least (or, alternatively, less than) minutes, hours, or days. Sequential administration also encompasses administration of a chosen antineoplastic agent followed by the administration of the adenoviral vector. The interval between administration may be in terms of at least (or, alternatively, less than) minutes, hours, or days.

Administration of the above-described methods may also include repeat doses or courses of target-cell specific adenovirus and chemotherapeutic agent depending, inter alia, upon the individual's response and the characteristics of the individual's disease. Repeat doses may be undertaken immediately following the first course of treatment (i.e., within one day), or after an interval of days, weeks or months to achieve and/or maintain suppression of tumor growth. A particular course of treatment according to the above-described methods, for example, combined adenoviral and chemotherapy, may later be followed by a course of combined radiation and adenoviral therapy.

Anti-neoplastic agents include those from each of the major classes of chemotherapeutics, including but not limited to: alkylating agents, alkaloids, antimetabolites, antitumor antibiotics, nitrosoureas, hormonal agonists/antagonists and analogs, immunomodulators, photosensitizers, enzymes and others. In some embodiments, the antineoplastic is an alkaloid, an antimetabolite, an antibiotic or an alkylating agent. In certain embodiments the antineoplastic agents include, for example, thiotepa, interferon alpha-2a, and the M-VAC combination (methotrexate-vinblastine, doxorubicin, cyclophosphamide). Preferred antineoplastic agents include, for example, 5-fluorouracil, cisplatin, 5-azacytidine, and gemcitabine. Particularly preferred embodiments include, but are not limited to, 5-fluorouracil, gemcitabine, doxorubicin, miroxantrone, mitomycin, dacarbazine, carmustine, vinblastine, lomustine, tamoxifen, docetaxel, paclitaxel or cisplatin. The specific choice of both the chemotherapeutic agent(s) is dependent upon, inter alia, the characteristics of the disease to be treated. These characteristics include, but are not limited to, location of the tumor, stage of the disease and the individual's response to previous treatments, if any.

In addition to the use of single antineoplastic agents in combination with a particular adenoviral vector, the invention also includes the use of more than one agent in conjunction with an adenoviral vector. These combinations of antineoplastics when used to treat neoplasia are often referred to as combination chemotherapy and are often part of a combined modality treatment which may also include surgery and/or radiation, depending on the characteristics of an individual's cancer. It is contemplated that the combined adenoviral/chemotherapy of the present invention can also be used as part of a combined modality treatment program.

There are a variety of delivery methods for the administration of antineoplastic agents, which are well known in the art, including oral and parenteral methods. There are a number of drawbacks to oral administration for a large number of antineoplastic agents, including low bioavailability, irritation of the digestive tract and the necessity of remembering to administer complicated combinations of drugs. The majority of parenteral administration of antineoplastic agents is intravenously, as intramuscular and subcutaneous injection often leads to irritation or damage to the tissue. Regional variations of parenteral injections include intra-arterial, intravesical, intra-tumor, intrathecal, intrapleural, intraperitoneal and intracavity injections.

Delivery methods for chemotherapeutic agents include intravenous, intraparenteral and introperitoneal methods as well as oral administration. Intravenous methods also include delivery through a vein of the extremities as well as including more site specific delivery, such as an intravenous drip into the portal vein of the liver. Other intraparenteral methods of delivery include direct injections of an antineoplastic solution, for example, subcutaneously, intracavity or intra-tumor.

Assessment of the efficacy of a particular treatment regimen may be determined by any of the techniques known in the art, including diagnostic methods such as imaging techniques, analysis of serum tumor markers, biopsy, the presence, absence or amelioration of tumor associated symptoms. It will be understood that a given treatment regime may be modified, as appropriate, to maximize efficacy.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

The following examples are offered by way of illustration and not by way of limitation.

EXPERIMENTAL

Example 1

Figure 2:
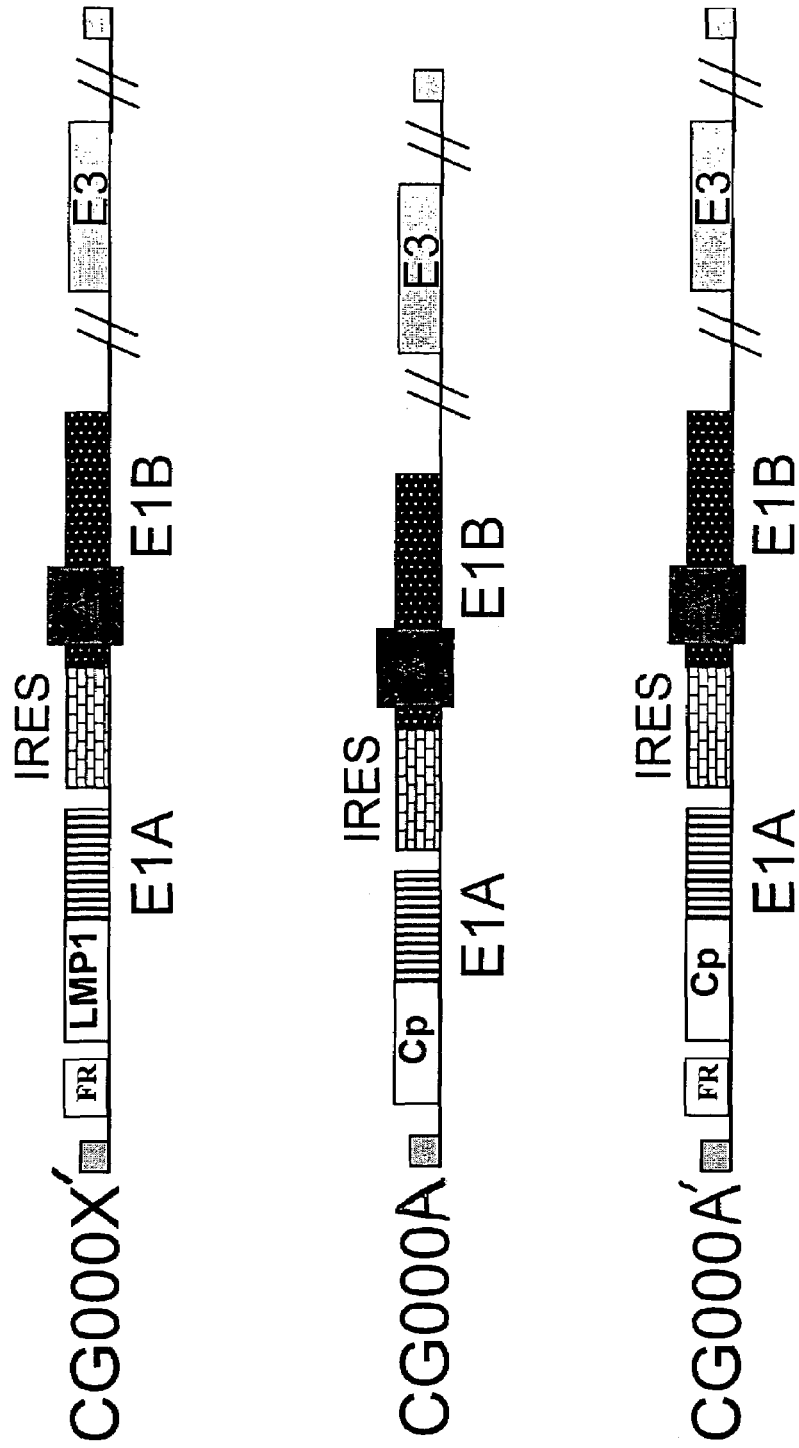
FIG. 2 depicts schematics of EBV-specific adenovirus vectors.

The adenoviruses are constructed using the protocols as set forth in Rodriguez at al, (1997) Cancer Res, 2559-2563, Yu, D-C et al, (1999) Cancer Res, 59, 1498-1504 (herein incorporated by reference). Constructs are as shown in FIGS. 1 and 2. In brief, the native adenovirus E1A promoter (present in CG8020), where the construct optionally contains an IRES sequence (shown as CG8840, and as described in co-pending patent application Ser. No. 09/814,292, herein incorporated by reference) is replaced by the promoters of the following genes: LMP1, LMP 2A, LMP 2B and Cp. The constructs are shown in FIG. 1 as CG000X; CG000Y; CG000Z; and CG000A, respectively.

Further the FP enhancer element is placed 5' of these promoters, as shown in CG000X' and CG000A'. The DNA fragment of these promoters is generated by PCR amplification from genomic DNA using specific primers. Similarly the IRES element in these viral constructs is replaced by the additional promoter elements that have been described in this application. Viruses will be made via transient transfection in 293 cells employing the left and right arm plasmids as described in above-mentioned publications.

It is evident from the above results that adenoviruses can be developed with specificity for particular host cells, where the viruses are replication-competent. The viruses may be vehicles for the introduction of a wide variety of genes into particular target cells.

The invention now being fully described, it will be apparent to one of ordinary skill in the art that many changes and modifications can be made thereto without departing from the spirit or scope of the appended claims.

What is claimed is:

1. A replication-competent adenovirus vector comprising a first adenovirus gene essential for replication under transcriptional control of an Epstein Barr-Virus (EBV)-specific transcriptional regulatory element (TRE) comprising a sequence selected from the group consisting of a sequence upstream of the translational start codon for the LMP1 gene, wherein said sequence is SEQ ID NO:1, a sequence upstream of the translational start codon for the LMP2A gene, wherein said sequence is SEQ ID NO:2 and the Cp promoter sequence which is SEQ ID NO:3.

2. The adenovirus vector according to claim 1, wherein said EBV-specific IRE comprises SEQ ID NO:1.

3. The adenovirus vector according to claim 1, wherein said EBV-specific TRE comprises SEQ ID NO:2.

4. The adenovirus vector according to claim 1, wherein said, EBV-specific TRE comprises the Cp promoter sequence, which sequence is SEQ ID NO:3.

5. The adenovirus vector according to claim 1, wherein said EBV-specific TRE further comprises the FR enhancer sequence, which sequence is SEQ ID NO:4.

6. The adenovirus vector according to claim 1, further comprising a second adenoviral gene co-transcribed under transcriptional control of said EBV-specific TRE.

7. The adenovirus vector of claim 1, wherein said first adenoviral gene essential for replication is E1A or E1B.

8. A composition comprising:
a replication-competent adenovirus vector according to claim 1 and a pharmaceutically acceptable excipient.

9. An isolated host cell comprising the adenovirus vector of claim 1.

10. The adenovirus vector according to claim 2, wherein said EBV-specific TRE comprises an ED-L1 regulatory region which is nucleotides 64 to 70 of SEQ ID NO:1.

11. The adenovirus vector according to claim 4, wherein said EBV-specific TRE further comprises the FR enhancer sequence, which sequence is SEQ ID NO:4.

12. A composition comprising:
a replication-competent adenovirus vector according to claim 5 and a pharmaceutically acceptable excipient.

13. An isolated host cell comprising the adenovirus vector of claim 5.

14. The adenovirus vector according to claim 6, wherein the second adenoviral gene is under translational control of an IRES.

15. The adenovirus vector of claim 7, wherein E1A or E1B has a mutation in, or deletion of, its endogenous promoter.

16. The adenovirus vector of claim 15, wherein E1B has a deletion of the 19-kDa region.

* * * * *

SEQUENCE LISTING

<160> NUMBER OF SEQ ID NOS: 4

<210> SEQ ID NO 1
<211> LENGTH: 575
<212> TYPE: DNA
<213> ORGANISM: Epstein Barr virus

<400> SEQUENCE: 1

```
tcagggcagt gtgtcaggag caaggcagtt gaggaaagaa gggggcagag cagtgtgaga      60
ggcttatgta gggcggctac gtcagagtaa cgcgtgtttc ttgggatgta ggcccggggg     120
gatttgcggg gtctgccgga ggcagtacgg gtacagattt cccgaaagcg gcggtgtgtg     180
tgtgcatgta agcgtagaaa ggggaagtag aaagcgtgtg tttgtgttag aaaagcgggt     240
ccccgggggg caagctgtgg gaatgcggtg gccaagtgca acaggaaatg gaaaggcagt     300
gcggcaatca gaaggggag tgcgtagtgt tgtgggaagc ggcagtgtaa tctgcacaaa      360
gaggcgcggg gcgcgcaacg ttgggaggtc gttggcggca ggcgggaggc cgtgctttag     420
gggggttcag gtgaggcaag gctgtggggt aaccgtaggg gaggcgggtg aggcggctaa     480
gagggctaag ggtcggcggg tgacgaagca gcagacggcg gatatgggaa tttcagaatg     540
aggtggcgga ttcaggcgaa aagggtgtgg gctgt                                575
```

<210> SEQ ID NO 2
<211> LENGTH: 545
<212> TYPE: DNA
<213> ORGANISM: Epstein Barr virus

<400> SEQUENCE: 2

```
cgcaccaact gcggcaaatg gcggtgttat gaaggaaaag gatgggagcc tctctgttgc      60
tgttgacctg tcacttccca agccctggca cctgccagtg acctgcgttg ggaaaaatga     120
caaggaggaa gcccacgggg tttatgtttc tggatacttg tcgcaataaa cgcacttgcc     180
tatttcacct tgttttagtg tggcattggg ggggtggcat tgcgggtgga tagcctcgcg     240
actcgtggga aaatgggcgg aagggcaccg tgggaaaata gttccaggtg acagcagcag     300
tgtgtgaaga ttgtcacagc tgctggtttg gagaaaacgg gggtgggcgg tgatcaggga     360
gaacaattcc ccggggacac ctgcacgaga cccctgggct ctcaggaact ccgcccaggt     420
cttgccaatt ggggtgatcc tgtagcgccg cggtttcagc atcacaggtt attttgcctg     480
aagcttgctg gggcgtaaat ccctctcgcc ttgtttctca gagagcattt caggccggtt     540
ttgca                                                                 545
```

<210> SEQ ID NO 3
<211> LENGTH: 1223
<212> TYPE: DNA
<213> ORGANISM: Epstein-Barr virus

<400> SEQUENCE: 3

```
aataaaatga aaccttttat tcttgattgc ctcttgtgtt cttgccgccc aggtaccttc      60
ctgtgttctc cccacgggaa aaagaatagc ttctgcagaa ggccattgac gcaagttttg     120
cccgtgggga ttacccgacc cagccactta cagcacattt tgttctaggt ccatcttagg     180
agcccgggcc agcattctat cagcttaacg ggaagagaag tggggagggc actcgcccac     240
taaccttaac acctgcagcc tacaaaagta cactagctgt ttgctctatt cgccactaga     300
gaccgccaag atgcgaaact acaggcccgg gcccaggcct tgcagggcag acggttaggc     360
tgacaagggg acaagtgtgg caggtgggcg ggaaggggca caagaatgcc ggcgaaactg     420
gaccacggtc caccccgccc tcaagcgtcc gggagccggg cggctcggct aaggagggcg     480
gccttgcgaa caattattag tagctaccaa caagggcccc cagatgcccc ccaccagtca     540
cccggccgtg tccactcaca tattccactc ttatttttaa attaatgtgt cccaattaga     600
```

```
                                     -continued aacccaagcg cagaaattag ttgagaggct agtgttttaa acatgcaccc taggccagcc    660
agagataatg tcacaagatt atcaagttgg tgtaaacacg ccgtgggaaa aaatttatgg    720
ttcagtgcgt cgagtgctat ctttggaaca gtagaaaatt gaaccttgtt ggcgggagaa    780
ggaataacgc cttatctggg aggagcgacg gattatagcc aataagagag ctcaagacgc    840
agggctcgca aagtatagtg gccccgtggg accttagagg tggagcaacg tctaaagtgg    900
taataacacc aggcggggct gggcaaaggg gtcctacggg cgggattaat tacgccttgc    960
ttacgcaagc tcagttaatt cgcccacgac ttgaaaaatg tagcccttaa ccaattggcg    1020
gcccctaagg gggggactaa ggtcccacta caaaaactct gtgttctgct gcaaattttta   1080 gatcagatgg catagagaca aggacaccga agaccccag agccctcatc gcagggttct     1140
taccatgcgg ccatgtaggc ccacttaaca ctacaagacc tacgcctctc cattcatcat    1200
gtaacccaca aatcatctaa acc                                            1223

<210> SEQ ID NO 4
<211> LENGTH: 622
<212> TYPE: DNA
<213> ORGANISM: Epstein Barr virus

<400> SEQUENCE: 4
gggtatcata tgctgactgt atatgcatga ggatagcata tgctacccgg atacagatta    60
ggatagcata tactacccag atatagatta ggatagcata tgctacccag atatagatta   120
ggatagccta tgctacccag atataaatta ggatagcata tactacccag atatagatta   180
ggatagcata tgctacccag atatagatta ggatagccta tgctacccag atatagatta   240
ggatagcata tgctacccag atatagatta ggatagcata tgctatccag atatttgggt   300
agtatatgct acccagatat aaattaggat agcatatact accctaatct ctattaggat   360
agcatatgct acccggatac agattaggat agcatatact acccagatat agattaggat   420
agcatatgct acccagatat agattaggat agcctatgct acccagatat aaattaggat   480
agcatatact acccagatat agattaggat agcatatgct acccagatat agattaggat   540
agcctatgct acccagatat agattaggat agcatatgct atccagatat ttgggtagta   600
tatgctaccc atggcaacat ta                                            622
```